United States Patent [19]

Hamminga et al.

[11] Patent Number: 5,066,649
[45] Date of Patent: Nov. 19, 1991

[54] 8,9-ANNELATED-1,2,3,4-TETRAHYDRO-β-CARBOLINE DERIVATIVES

[75] Inventors: Derk Hamminga; Ineke van Wijngaarden; Johannes W. C. M. Jansen, all of Weesp, Netherlands

[73] Assignee: Duphar International Research B.V., Weesp, Netherlands

[21] Appl. No.: 465,460

[22] Filed: Jan. 16, 1990

[30] Foreign Application Priority Data

Jan. 19, 1989 [NL] Netherlands ............... 8900120

[51] Int. Cl.⁵ ............... A61K 31/33; A61K 31/38; C07D 267/22; C07D 487/00
[52] U.S. Cl. ............... 514/183; 514/431; 540/468; 540/476
[58] Field of Search ............... 540/468, 476; 514/431, 514/183

[56] References Cited

U.S. PATENT DOCUMENTS 3,914,421 10/1975 Rajagopalan ............... 424/248
4,782,061 1/1988 Kruse et al. ............... 514/254

FOREIGN PATENT DOCUMENTS 0189612 8/1986 European Pat. Off. .
320075 6/1989 European Pat. Off. .

OTHER PUBLICATIONS

*Lysis of Clots Prepared from Whole Blood and Plasma,* Fletcher B. Taylor et al., Federation Proceedings 40 pp. 2092–2098 (1981).
*Culture of Arterial Endothelial Cells,* F. M. Booyse et al., Thrombos. Diathes. Haemorrh. (Stuttg.), pp. 825–839 (1975).
*Evidence for the Occurrence of a Fast–Acting Inhibitor for Tissue–Type Plasminogen Activator in Human Plasma,* J. H. Verheijen et al., Thromb Haemostas (Stuttgart) 51 (3) pp. 392–395 (1984).
*A. Tetrahydrocarbolines,* Advances in Heterocyclic Chemistry 3, pp. 83–91 (1964).
*Some 5,6-Dihydro-4H-Pyrrolo[3,2,1-i,j]Quinolines,* Heterocyclic Chemistry II, pp. 387–393 (1974).
*The Preparation of 3,4-Dihydroisoquinolines and Related Compouds,* Wilson et al., Organic Reaction 6, pp. 74–80 (1951).
Chemical Abstracts 112 20979k.
Chemical Abstracts 84 59411x.
Chemical Abstracts 111 77986u.

*Primary Examiner*—Mukund J. Shah
*Assistant Examiner*—Matthew V. Grumbling
*Attorney, Agent, or Firm*—Stevens, Davis, Miller & Mosher

[57] ABSTRACT

The invention relates to a new group of 8,9-annelated-1,2,3,4-tetrahydro-β-carbolines of the formula

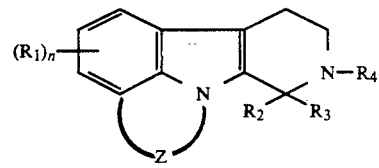

and the salts and prodrugs thereof. The meanings of $R_1$, n, Z, $R_2$, $R_3$, and $R_4$ are defined within the body of the specification.

It has been found that the compounds have good fibrinolytic properties and can be used in particular as orally active fibrinolytics.

3 Claims, No Drawings

8,9-ANNELATED-1,2,3,4-TETRAHYDRO-β-CARBOLINE DERIVATIVES

The invention relates to a group of new 8,9-annelated-1,2,3,4-tetrahydro-β-carboline derivatives and salts and prodrugs thereof, to the preparation of said compounds and to pharmaceutical compositions which comprise at least one of these compounds as an active substance.

It has been found surprisingly that the compounds of formula 1

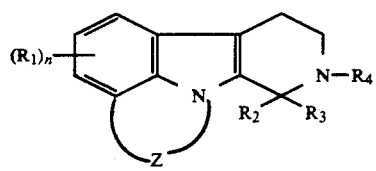

and the salts and prodrugs thereof have good fibrinolytic properties and may be used in particular as orally active fibrinolytics.

The symbols in the above formula 1 have the following meanings:

$R_1$ is straight or branched alkyl having 1-3 C-atoms, or is straight or branched alkoxy or alkylthio having 1-4 C-atoms, or $R_1$ is a group $R_5R_6N-CO-$ wherein $R_5$ and $R_6$ independently of each other are hydrogen, alkyl having 1-3 C-atoms, or together with the nitrogen atom constitute a heterocyclic 5- or 6-ring, or $R_1$ is hydroxy, halogen, cyano, trifluoromethyl;

n has the value 0 or 1;

Z, together with the two carbon atoms and the nitrogen atom, constitutes a heterocyclic group which consists of 9-12 ring atoms and which, in addition to the nitrogen atom already present, may comprise a sulfur atom as a second hetero atom and which group may be substituted with 1-4 methyl groups or with a spiroalkyl group;

$R_2$ is hydrogen, straight or branched alkyl having 1-8 C-atoms, alkenyl or alkynyl having 2-8 C-atoms, which groups may be substituted with one or more fluorine atoms, with a phenyl group which may be substituted with a halogen atom, an alkyl group having 1-3 C-atoms, methoxy or trifluoromethyl, or with the cyclopropyl group or $R_2$ is cycloalkyl having 3-8 C-atoms which may be substituted with one or more alkyl groups having 1-4 C-atoms, or $R_2$ is cycloalkenyl having 5-7 C-atoms, or $R_2$ is a phenyl group substituted with 0-2 groups $R_7$, wherein $R_7$ is straight or branched alkyl having 1-4 C-atoms which may be substituted with one or more fluorine atoms, or two alkyl groups $R_7$ bound to adjacent carbon atoms constitute a ring annelated to the phenyl group and consisting of 5-7 C-atoms, or $R_7$ is cycloalkyl, cycloalkoxy or cycloalkylthio having 3-7 C-atoms, or $R_7$ is straight or branched alkoxycarbonyl having 1-4 C-atoms in the alkoxy group, or $R_7$ is halogen or hydroxy;

$R_3$ is hydrogen or straight or branched alkyl having 1-6 C-atoms; and $R_4$ is hydrogen, straight or branched alkyl having 1-4 C-atoms.

Suitable acids with which the compounds of formula 1 according to the invention may form pharmaceutically acceptable acid addition salts are, for example, hydrochloric acid, sulphuric acid, phosphoric acid, nitric acid, and organic acids, for example, citric acid, fumaric acid, maleic acid, tartaric acid, acetic acid, benzoic acid, p-toluene sulphonic acid, methane sulphonic acid, and the like.

When the symbols $R_2$ and $R_3$ have different meanings and/or when the group Z, together with the two carbon atoms and the nitrogen atom, constitute(s) a ring which is substituted, the compounds of formula 1 may comprise one or more chiral centers. The invention relates both to racemates and individual enantiomers.

The invention also relates to prodrugs of the compounds of formula 1, i e. derivatives of the said compounds which as such are inactive, from which, after splitting off an easily removable group, for example, an ester group or an ether group, an active compound of formula 1 is obtained.

The carboline derivatives according to the invention are orally active fibrinolytics and may therefore be used in the control of already formed venous or arterial thrombi or may be administered to prevent thrombi. The compounds may be used, for example, for a short period of time during operations, or for a long period of time in enhanced risk, for example, after myocardial infarction, cerebral or peripheral suffering. The best compounds are possibly active via an increase of the tissue plasminogen activator activity, as a result of which the possibility of spontaneous bleedings can be prevented.

The oral fibrinolytic activity of the compounds according to the invention was established in the first instance in the so-called DBCLT (diluted blood clot lysis test; Taylor F. B et al, Fed. Proc. (1981), 40, 2092-2098). Rats are treated orally with the compound to be tested. After 1-3 hours blood is taken. $^{125}$I-labelled fibrinogen and thrombine are added, as a result of which a blood clot is formed which, depending on the extent of fibrinolytic activity caused by the compound to be tested, dissolves more rapidly as compared with blood clots of untreated animals.

The increase of the tissue plasminogen activator activity was measured in cultures of endothelium cells (Thrombosis Diathesis Haemorrhagis (Stuttgart), 34, (1975), pp. 825-839; and Thrombosis and Haemostasis, 51, (1984), p. 392).

A few of the compounds belonging to the invention have psychotropic activity, for example, antiaggressive or antipsychotic. These activities were found in the tests mentioned in Netherlands Patent Applications 8403917 and 8403918, corresponding to EP 189,612 and U.S. Pat. No. 4,782,061, respectively.

The pharmacologically active compounds of the present invention, their salts and prodrugs can be brought into forms suitable for administration, for example, pills, tablets, coated tablets, capsules, powders, injection liquids, and the like, by means of the techniques conventionally used for this purpose and while using suitable auxiliary substances, for example, solid or liquid carrier materials.

The dosage in which the compounds according to the invention may be used depends on the nature and the severity of the disease to be treated and on the mode of administration.

The compounds of formula 1 can be prepared in at least one of the following manners depending on the meaning of the symbols:

a) analogous to the method described in Advances in Heterocyclic Chemistry, vol. 3, pp. 79-207 (The Carbolines).

More in particular compounds of this type can be obtained in a good yield by reaction of a compound of formula 2

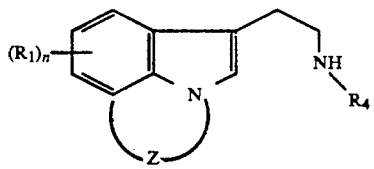
(2)

wherein $R_1$, $R_4$, n and Z have the above-mentioned meanings, or a salt thereof, with a carbonyl compound of formula 3

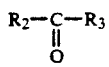
(3)

wherein $R_2$ and $R_3$ have the above-mentioned meanings. The reaction is preferably carried out in a suitable solvent, for example, acetic acid, alcohol, etc., at a temperature between 10° and 120° C.

The starting compounds of formula 2 required for this mode of preparation can be obtained in a manner known for the synthesis of analogous compounds, for example, by reaction of a compound of formula 4

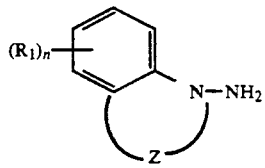
(4)

with a compound of the formula 5 or 6

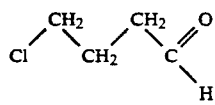
(5)

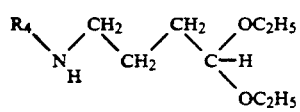
(6)

in which formulae $R_1$, $R_4$, n and Z have the above mentioned means (see also Khimiya Geterotsiklicheskikh Soedineii, (1973), pp. 213-218 and J. Heterocyclic Chem. 11, (1974), pp. 387-393).

The hydrazines of formula 4 required for this reaction may be prepared inter alia by nitrosation and subsequent reduction of the corresponding compounds of formula 7

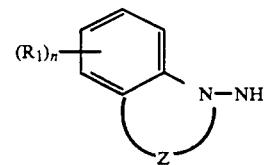
(7)

wherein $R_1$, n and Z have the above-mentioned meanings; good methods for the preparation of compounds of formula 7 are, for example, i) if Z is the group —CH$_2$—Z'—CH$_2$—, wherein Z' together with the two —CH$_2$—groups is the above mentioned group Z, by oxidation and subsequent reduction of 2,3-annelated indoles according to the reaction equation

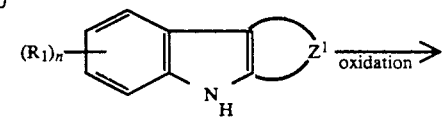

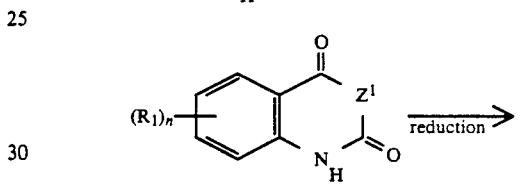

ii) for the group —Z"—CH$_2$—, wherein Z" together with the —CH$_2$— group is the above-mentioned group Z, by Schmidt-reaction and subsequent reduction of the resulting lactam according to the reaction equations

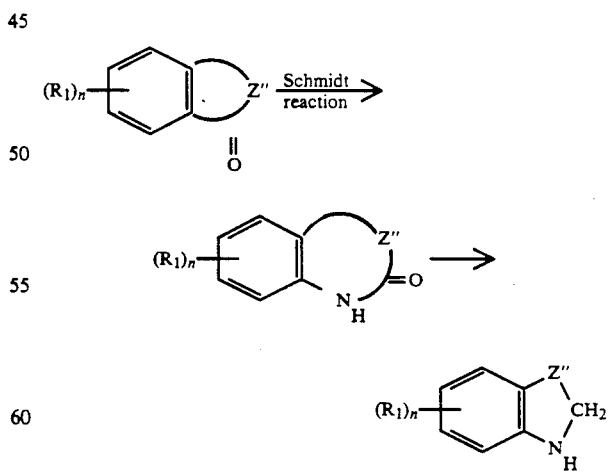

b) the compounds of formula 1, wherein $R_1$, $R_2$, and Z have the above mentioned meanings and wherein $R_3$ and $R_4$ are a hydrogen atom, can be prepared in a good yield by reduction of the analogous starting compounds of formula 8

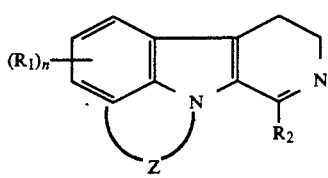

(8)

with a suitable reducing agent, for example, hydrogen, by means of a catalyst. The starting compounds of formula 8 can be obtained in a good yield by Bischler-Napieralski ring closure of a compound of formula 9

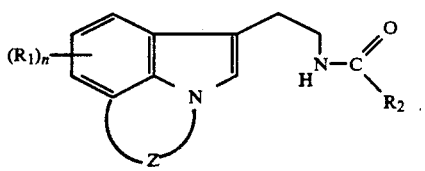

(9)

Suitable methods for Bischler-Napieralski ring closures are described inter alia in Organic Reactions, Vol. VI, p. 74.

c) the compounds of formula 1 wherein $R_4$ has a meaning different from hydrogen, can be obtained in a good yield by reacting the analogous compound, wherein $R_4$ is H, in a manner known per se with a compound $R_4$ - Y, wherein Y is a reactive group, for example, halogen, ethoxycarbonyloxy, or acetoxy.

The invention will now be described in greater detail with reference to the ensuing specific example.

11-cyclolhexyl-4,5,6,7,8,9,11,12,13,14-decahydropyrido-[4', 3':4.5]pyrrolo[3,2,1-1m][1]benzazonine hydrochloride a) 15.0 g (85.1 mmol) of 2,3,4,5,6,7 hexahydro-1H-1-benzazonine were added to a mixture of 14 ml of concentrated sulfuric acid in 53 ml of water and 35 ml of methylene chloride under a nitrogen atmosphere. The mixture was cooled to −5° C. and a solution of 5 g (85.1 mmol) of sodium nitrite in 37 ml of water was added dropwise while stirring at maximally 0° C. The mixture was then stirred at 0° C. for another hour. The methylene chloride layer was separated, dried and evaporated in vacuo. In this manner 17.2 g (=98%) of a brown oil were obtained.

b) 17.0 g (83.3 mmol) of the above final product were dissolved in 78 ml of dry tetrahydrofuran and added dropwise under a nitrogen atmosphere to a boiling suspension of 6.3 g (166.6 mmol) of lithium aluminium hydride in 157 ml of tetrahydrofuran. The reaction mixture was then boiled for 1 hour. It was then cooled and 6.3 ml of water, 12.6 ml of 2 N sodium hydroxide and 12.6 ml of water were successively added dropwise. The mixture was then boiled for 15 minutes, cooled and filtrated. The filtrate was evaporated in vacuo. In this manner 15.3 g of the crude 1-amino 2,3,4,5,6, 7-hexahydro-1H-1-benzazonine were obtained. This product was sufficiently pure for further reactions.

c) The final product of b) (15.3 g) was dissolved in a mixture of 160 ml of methanol and 16 ml of water. 9.4 g of 4-chlorobytyraldehvde were added and the mixture was boiled for 16 hours. It was then evaporated in vacuo. The residue was shaken with a mixture of methylene chloride and 2 N sodium hydroxide. The methylene chloride layer was separated and evaporated in vacuo. The residue was purified by means of flash chromatography using methylene chloride/methanol/ammonia 92.5/7/0.5 as an eluent. After evaporating the good fractions, 11.0 g of 1-(2-aminoethyl)4,5,6,7,8, 9-hexahydropyrrolo[3,2,1-1m][1]benzazonine were obtained.

d) 1.5 g (6.2 mmol) of the above final product, together with 0.69 g (6.2 mmol) of cyclohexylcarboxaldehyde, were dissolved in 30 ml of acetic acid and heated at 40° C. for 48 hours. The mixture was then evaporated in vacuo and shaken with methylene chloride and 2N sodium hydroxide. The methylene chloride layer was separated, evaporated and chromatographed over silica gel using methylene chloride/methanol (95/5) as an eluent. The good fractions were evaporated in vacuo. The residue was dissolved in ethyl acetate, after which alcoholic hydrochloric acid was added. 1.51 g (65%) of the desired hydrochloride having a melting-point of 253°-254° C. were obtained in this manner. The following compounds were obtained in an analogous manner:

a) 11-(1-fluoro-ethylene)-4,5,6,7,8,9,11,12,13,14-decahydropyrido[4',3':4,5]pyrrolo[3,2,1-1m][1]benzazonine hydrochloride, melting-point 233°-234° C.;

b) 12-(4-isopropylphenyl)-5,6,7,8,9,10,12,13,14,15-decahydro-4H-pyrido[4',3':4,5]pyrrolo[3,2,1-mn][1]benzazecine hydrochloride, melting point 209°-209.5° C.

We claim:

1. A compound of formula 1

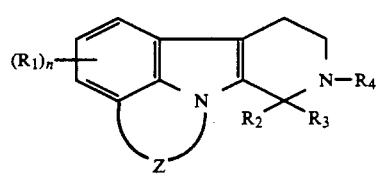

(1)

wherein $R_1$ is straight or branched alkyl having 1–3 carbon atoms, straight or branched alkoxy or alkylthio having 1–4 carbon atoms, a group of the formula $R_5T_6N$—CO— wherein $R_5$ and $R_6$ independently of each other are hydrogen, alkyl having 1–3 carbon atoms or together with the nitrogen atom, form a heterocyclic 5- or 6-membered ring, hydroxy, halogen, cyano or trifluoromethyl;

n has the value 0 or 1;

Z, together with the two carbon atoms and the nitrogen atom, forms a heterocyclic group which consists of 9-12 ring atoms and which, in addition to the nitrogen atom already present, may comprises a sulfur atom as a second hetero atom, said heterocyclic group being unsubstituted or substituted by 1–4 methyl groups;

$R_2$ is hydrogen, or is selected from the group consisting of straight or branched alkyl having 1–8 carbon atoms, or alkenyl or alkynyl having 2–8 carbon atoms, said group being unsubstituted or substituted by one or more fluorine, with a phenyl group which is unsubstituted or substituted by halogen, alkyl having 1–3 carbon atoms, methoxy or trifluoromethyl, or cyclopropyl, or $R_2$ is cycloalkyl having 3–8 carbon atoms which is unsubstituted or substituted by one or more alkyl groups having 1–4 carbon atoms, or $R_2$ is cycloalkenyl having 5–7 carbon atoms or phenyl which is substituted by 0–2 $R_7$ groups, wherein $R_7$ is straight or branched alkyl having 1-4 carbon atoms which is unsubstituted or substituted by one or more fluorine atoms or two $R_7$ groups bound to adjacent carbon atoms form a ring annelated to the phenyl group and consist of 5-7 carbon atoms or $R_7$ is cycloalkyl, cycloalkoxy or cycloalkylthio having 3-7 carbon atoms, straight or branched alkoxycarbonyl having 1-4 carbon atoms in the alkoxy group, halogen or hydroxy;

$R_3$ is hydrogen or straight or branched alkyl having 1-6 carbon atoms; and $R_4$ is hydrogen or straight or branched alkyl having 1-4 carbon atoms; or a pharmacologically acceptable salt or prodrug thereof.

2. A pharmaceutical composition having fibrinolytic activity comprising a fibrinolytically effective amount of a compound of claim 1 and a pharmaceutically acceptable carrier.

3. A method of dissolving and preventing blood clots comprising administering to a patient a fibrinolytically effective amount of a compound of claim 1.

* * * * *